(12) United States Patent
Wang

(10) Patent No.: US 10,473,635 B2
(45) Date of Patent: Nov. 12, 2019

(54) DETECTING APPARATUS AND VOLATILE ORGANIC COMPOUND DETECTOR

(71) Applicant: MIRLE AUTOMATION CORPORATION, Hsinchu (TW)

(72) Inventor: Jing-Tang Wang, Hsinchu (TW)

(73) Assignee: MIRLE AUTOMATION CORPORATION, Hsinchu (TW)

( * ) Notice: Subject to any disclaimer, the term of this patent is extended or adjusted under 35 U.S.C. 154(b) by 152 days.

(21) Appl. No.: 15/818,115

(22) Filed: Nov. 20, 2017

(65) Prior Publication Data

US 2018/0164269 A1    Jun. 14, 2018

Related U.S. Application Data

(60) Provisional application No. 62/433,846, filed on Dec. 14, 2016.

(30) Foreign Application Priority Data

Feb. 24, 2017  (TW) .............................. 106106449 A

(51) Int. Cl.
*G01N 33/00* (2006.01)
*G01D 11/02* (2006.01)

(52) U.S. Cl.
CPC ..... *G01N 33/0047* (2013.01); *G01N 33/0029* (2013.01); *G01N 33/0049* (2013.01);
(Continued)

(58) Field of Classification Search
CPC .......... G01N 33/0029; G01N 33/0047; G01N 33/0049; G01N 15/06; Y02A 50/235; B08B 5/02
See application file for complete search history.

(56) References Cited

U.S. PATENT DOCUMENTS

| | | | |
|---|---|---|---|
| 2002/0016004 A1* | 2/2002 | Nguyen ................. | B01D 53/30 436/39 |
| 2009/0241684 A1* | 10/2009 | Matsuba .................. | G01P 5/02 73/861 |

(Continued)

FOREIGN PATENT DOCUMENTS

| CN | 102841047 A | 12/2012 |
|---|---|---|
| CN | 104792942 A | 7/2015 |

(Continued)

*Primary Examiner* — Herbert K Roberts
(74) *Attorney, Agent, or Firm* — Li & Cai Intellectual Property (USA) Office

(57) ABSTRACT

A detecting apparatus includes a detecting carrier and a detecting device. The detecting carrier can be moved into a charging frame or anyone of storing frames of a stock room. The detecting device is installed in the detecting carrier and includes a power module and a detector for volatile organic compounds (VOC). The power module is configured to supply power for operating the detecting apparatus. The detector includes a chassis, a displacement unit disposed in the chassis, a detecting unit disposed on the displacement unit, and a blowing unit disposed on the chassis. The detecting unit is configured to detect a concentration of VOC corresponding in position to the detecting carrier. The detecting unit can be arranged inside or outside the chassis by using the displacement unit. The blowing unit is configured to blow VOC adhered to the detecting unit.

10 Claims, 15 Drawing Sheets

(52) U.S. Cl.
CPC ............ *G01D 11/02* (2013.01); *Y02A 50/235* (2018.01); *Y02A 50/249* (2018.01)

(56) References Cited

U.S. PATENT DOCUMENTS

| | | | | |
|---|---|---|---|---|
| 2010/0274513 A1* | 10/2010 | Matsuba | ................ | G01D 9/005 |
| | | | | 702/89 |
| 2011/0114511 A1 | 5/2011 | Sjong | | |
| 2012/0046881 A1 | 2/2012 | Cannon | | |
| 2014/0182359 A1* | 7/2014 | Li | ........................ | G01N 15/082 |
| | | | | 73/38 |
| 2014/0230522 A1* | 8/2014 | Uemura | ................. | G01N 15/06 |
| | | | | 73/28.01 |
| 2018/0120278 A1* | 5/2018 | Hoorfar | ............. | G01N 33/0031 |

FOREIGN PATENT DOCUMENTS

| | | |
|---|---|---|
| JP | 3212366 U | 9/2017 |
| JP | 3213717 U | 11/2017 |
| JP | 2018096968 A | 6/2018 |
| TW | M480068 U | 6/2014 |

\* cited by examiner

DETECTING APPARATUS AND VOLATILE ORGANIC COMPOUND DETECTOR

BACKGROUND OF THE INVENTION

1. Field of the Invention

The present disclosure relates to a detecting apparatus; in particular, to a detecting apparatus and a volatile organic compound (VOC) detector for detecting volatile organic compounds.

2. Description of Related Art

A conventional detecting apparatus can be used to automatically detect particles in a stock room which is located between two working stations of a panel factory for transiting or temporarily storing semi-finished products, so that the semi-finished products can be confirmed being located in a clean space environment. However, the conventional detecting apparatus is provided without any VOC detector, so that the conventional detecting apparatus cannot be used to detect volatile organic compounds. In addition, after a conventional VOC detector runs a detecting process, the conventional VOC detector cannot remove the volatile organic compounds adhered thereto by itself, so that the follow-up detecting process of the conventional VOC detector is not carried out accurately.

SUMMARY OF THE INVENTION

The present disclosure provides a detecting apparatus and a VOC detector to effectively improve the drawbacks associated with conventional detecting apparatus and conventional VOC detectors.

The present disclosure discloses a detecting apparatus for being movably arranged in a stock room having a charging frame and a plurality of storing frames. The detecting apparatus includes a detecting carrier and a detecting device. The detecting carrier is configured for being transported into the charging frame or anyone of the storing frames. The detecting device is installed in the detecting carrier and includes a power module and a detecting module. The power module is configured to provide electricity for operating the detecting apparatus. The detecting module includes a volatile organic compound (VOC) detector. The VOC detector includes a chassis, a displacement unit, a detecting unit, and a blowing unit. The displacement unit is disposed in the chassis. The detecting unit is disposed on the displacement unit and configured to detect the concentration of volatile organic compounds corresponding in position to the detecting carrier, wherein the detecting unit is movable to be arranged inside or outside the chassis by using the displacement unit. The blowing unit is disposed on the chassis, wherein the blowing unit is configured to blow the detecting unit for removing at least part of volatile organic compounds adhered to the detecting unit.

The present disclosure also discloses a volatile organic compound (VOC) detector, which includes a chassis, a displacement unit, a detecting unit, and a blowing unit. The displacement unit is disposed in the chassis. The detecting unit is disposed on the displacement unit and configured to detect the concentration of volatile organic compounds. The detecting unit is movable to be arranged inside or outside the chassis by using the displacement unit. The blowing unit is disposed on the chassis, wherein the blowing unit is configured to blow the detecting unit for removing at least part of volatile organic compounds adhered to the detecting unit.

In summary, the detecting apparatus in the present disclosure is provided with the VOC detector for detecting the concentration of volatile organic compounds in the stock room. Moreover, after each detecting process of the VOC detector is implemented, the volatile organic compounds adhered to the VOC detector can be approximately removed by the blowing unit, thereby improving the accuracy of the follow-up detecting process of the detecting unit.

In order to further appreciate the characteristics and technical contents of the present disclosure, references are hereunder made to the detailed descriptions and appended drawings in connection with the present disclosure. However, the appended drawings are merely shown for exemplary purposes, and should not be construed as restricting the scope of the present disclosure.

DETAILED DESCRIPTION OF THE PREFERRED EMBODIMENTS

Reference is made to FIGS. 1 to 15, which illustrate an embodiment of the present disclosure. References are hereunder made to the detailed descriptions and appended drawings in connection with the present disclosure. However, the appended drawings are merely provided for exemplary purposes, and should not be construed as restricting the scope of the present disclosure.

Figure 1:
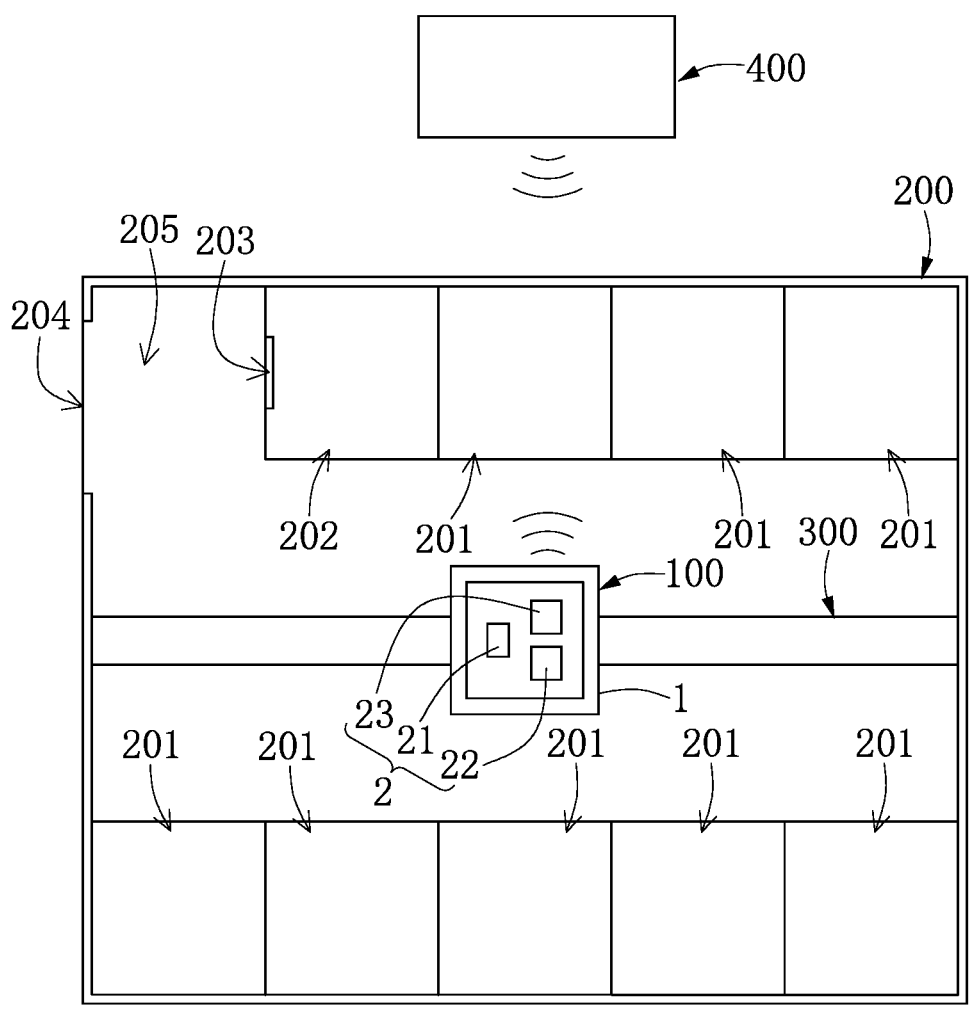
FIG. 1 is a schematic view showing a particle counter system according to the present disclosure.
Figure 2:
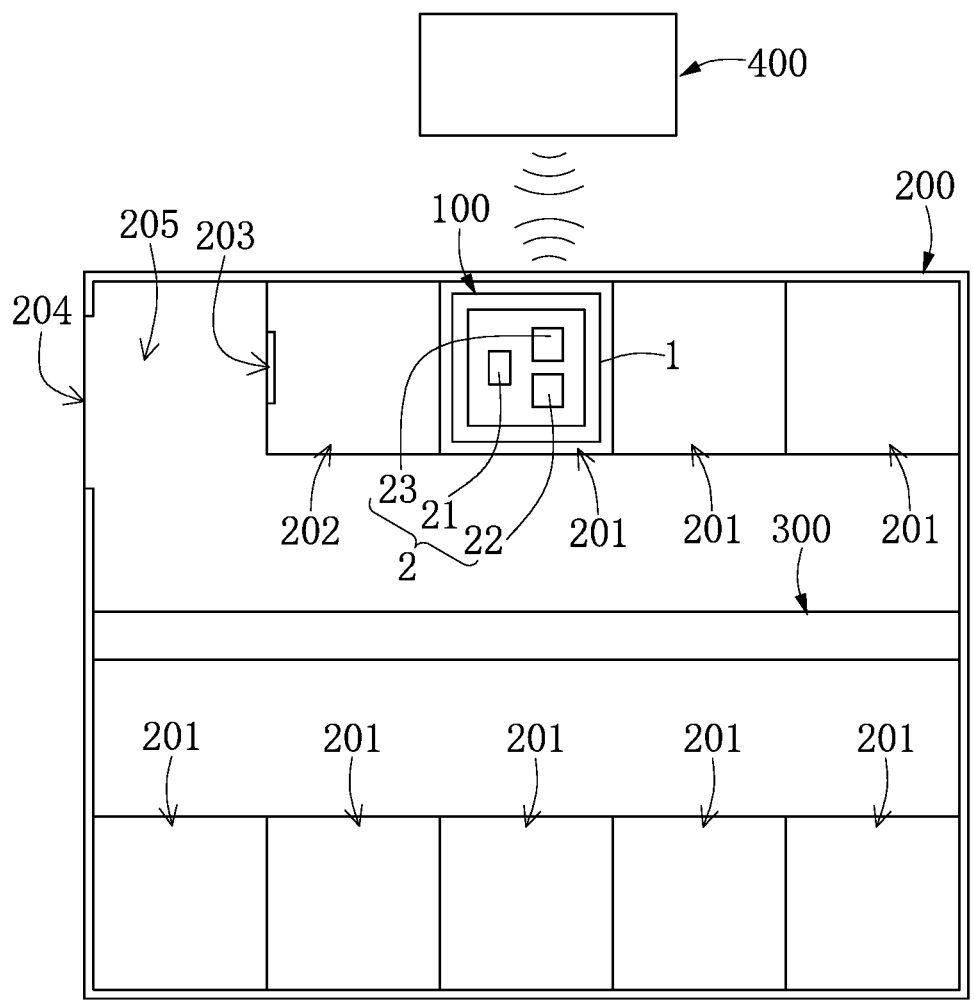
FIG. 2 is a schematic view showing a detecting apparatus of FIG. 1 in a detecting mode.
Figure 3:
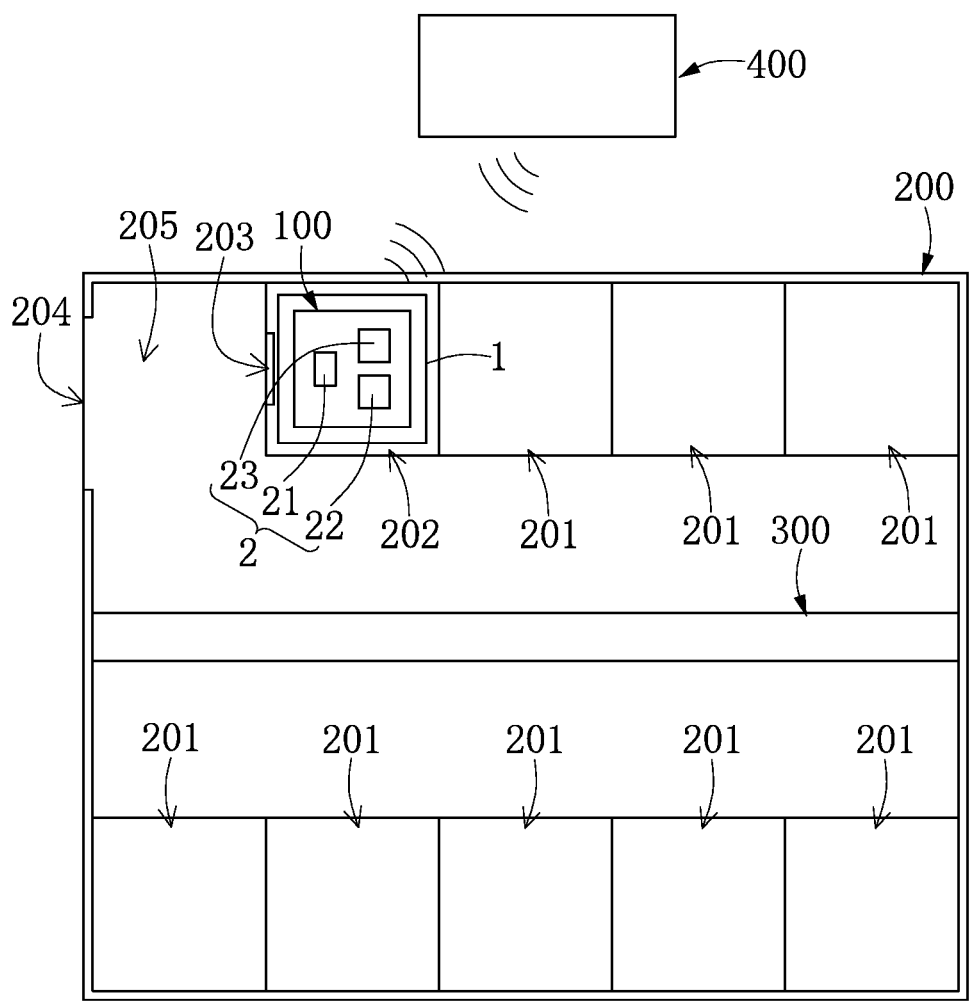
FIG. 3 is a schematic view showing the detecting apparatus of FIG. 1 in a charging mode.

Reference is first made to FIGS. 1 to 3, which illustrate a particle counter system 1000 of the present embodiment. The particle counter system 1000 in the present embodiment is preferably applied to a panel factor, but the present disclosure is not limited thereto. The particle counter system 1000 includes a stock room 200, a transporting apparatus 300, a detecting apparatus 100, and a controlling apparatus 400. It should be noted that the detecting apparatus 100 can be independently used or can be applied to other systems, that is to say, the detecting apparatus 100 in the present disclosure is not limited to the present embodiment.

The stock room 200 in the present embodiment is located between two working stations of a panel factory for transiting or temporarily storing semi-finished products (i.e., glass), but the present disclosure is not limited thereto. The stock room 200 includes a plurality storing frames 201, a charging frame 202, and a charging module 203 installed in the charging frame 202. The charging frame 202 and each of the storing frames 201 have the same structure. The storing frame 201 is used to accommodate a transporting carrier (not shown) which carries at least one semi-finished product. The charging frame 202 is used to accommodate the detecting apparatus 100, which needs to be charged, and the charging frame 202 is not used to accommodate any transporting carrier.

Moreover, the stock room 200 has at least one entrance 204. The charging frame 202 is arranged adjacent to the entrance 204, and the charging module 203 is mounted on a portion of the charging frame 202 arranged adjacent to the entrance 204. The stock room 200 has a clearance region 205 between the entrance 204 and the charging frame 202, and each of the storing frames 201 is not disposed on the clearance region 205.

The transporting apparatus 300 in the present embodiment can be an auto-guided vehicle and corresponding tracks, and at least part of the transporting apparatus 300 is arranged in the stock room 200. The transporting apparatus 300 is configured to transport the transporting carrier to anyone of the storing frames 201. The transporting apparatus 300 is also configured to transport the detecting apparatus 100 to the charging frame 202 or anyone of the storing frames 201. That is to say, the detecting apparatus 100 in the present embodiment is moved by using the transporting apparatus 300.

The detecting apparatus 100 is arranged in the stock room 200 and includes a detecting carrier 1 and a detecting device 2 installed in the detecting carrier 1. The detecting carrier 1 and the transporting carrier have the same structure, but the detecting carrier 1 is not used for carrying any semi-finished product. Accordingly, the detecting carrier 1 can enter into the charging frame 202 (as shown in FIG. 3) or anyone of the storing frames 201 (as shown in FIG. 2) by using the transporting apparatus 300.

Moreover, the detecting device 2 can be moved into anyone of the storing frames 201 by the movement of the detecting carrier 1, thereby detecting environment information of the corresponding storing frame 201, which is corresponding in position to the detecting carrier 1. The detecting device 2 includes a power module 21, a detecting module 22, and a wireless communication module 23. The power module 21 is configured to provide electricity for operating the detecting apparatus 100. The detecting module 22 is configured to detect the environment information corresponding in position to the detecting carrier 1. The wireless communication module 23 is configured to emit an electricity signal according to the electricity of the power module 21 and is configured to emit an environment signal according to the environment information of the detecting module 22.

The controlling apparatus 400 is wirelessly connected to the detecting apparatus 100 and the transporting apparatus 300. The controlling apparatus 400 is configured to receive the electricity signal and the environment signal emitted from the wireless communication module 23. The controlling apparatus 400 is configured to emit a controlling signal to the wireless communication module 23 according to the electricity signal so as to instruct the detecting apparatus 100 to be in one of a detecting mode and a charging mode. When the detecting apparatus 100 is in the charging mode, the detecting carrier 1 enters into the charging frame 202 by the transporting apparatus 300, and the charging module 203 is operated to charge the power module 21. When the detecting apparatus 100 is in the detecting mode, the detecting carrier 1 randomly enters into one of the storing frames 201 by the transporting apparatus 300, and the detecting module 22 is operated to detect the environment information.

Specifically, when the detecting apparatus 100 is operated and the power module 21 is in a low-electricity mode, the wireless communication module 23 transmits a low-electricity signal to the controlling apparatus 400, such that the controlling apparatus 400 emits a charging signal to the detecting apparatus 100 to instruct the detecting apparatus 100 to enter into the charging frame 202 for being charged, and then the detecting apparatus 100 is in the charging mode. Moreover, after the power module 21 of the detecting apparatus 100 is charged, the wireless communication module 23 transmits a full-electricity signal to the controlling apparatus 400, such that the controlling apparatus 400 emits a detecting signal to the detecting apparatus 100 to instruct the detecting apparatus 100 to randomly enter into one of the storing frames 201 for detecting, and then the detecting apparatus 100 is in the detecting mode.

Thus, when the power module 21 is in a low-electricity mode, the controlling apparatus 400 can immediately instruct the detecting apparatus 100 to be charged, so that the detecting apparatus 100 is charged without requiring any manual operation, and a staff does not need to enter into the stock room 200 for avoiding the stock room 200 being contaminated. Moreover, the charging frame 202 in the present embodiment is arranged adjacent to the entrance 204 of the stock room 200, thereby being beneficial for a staff to do the maintenance work for the charging frame 203 or the detecting apparatus 100.

In addition, the charging frame 202 and each of the storing frames 201 have the same structure, so that anyone of storing frames in the conventional stock room can be selected to be the charging frame 202, thereby easily applying the particle counter system 100 to the conventional stock room without changing the arrangement of the storing frames in the conventional stock room. Moreover, the detecting carrier 1 and the transporting carrier have the same structure, so that the detecting carrier 1 and the transporting carrier can be transported by the same transporting apparatus 300. That is to say, the particle counter system 1000 in the present embodiment can be operated by using the conventional transporting apparatus in the conventional stock room.

Specifically, the detecting apparatus 100 in the present embodiment is charged by the non-contacting charging frame 202, that is to say, when the detecting carrier 1 enters into the charging frame 202, the charging module 203 and the power module 21 are spaced away from each other, and the charging module 203 is operated to charge the power module 21 without contacting each other. The following description discloses the possible structure of the particle counter system 1000, but the present disclosure is not limited thereto.

Figure 4:
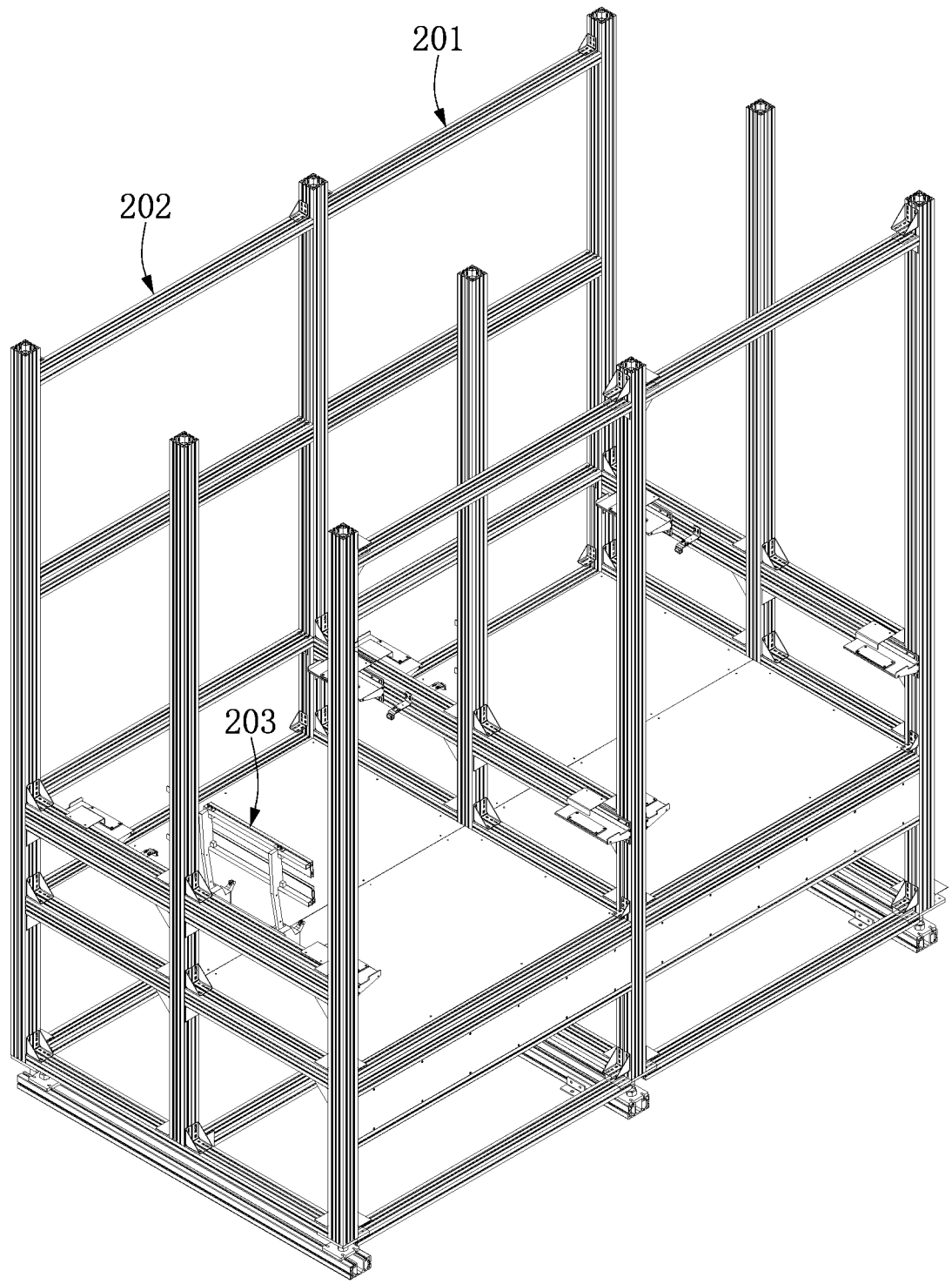
FIG. 4 is a perspective view showing a part of a stock room of the particle counter system.
Figure 5:
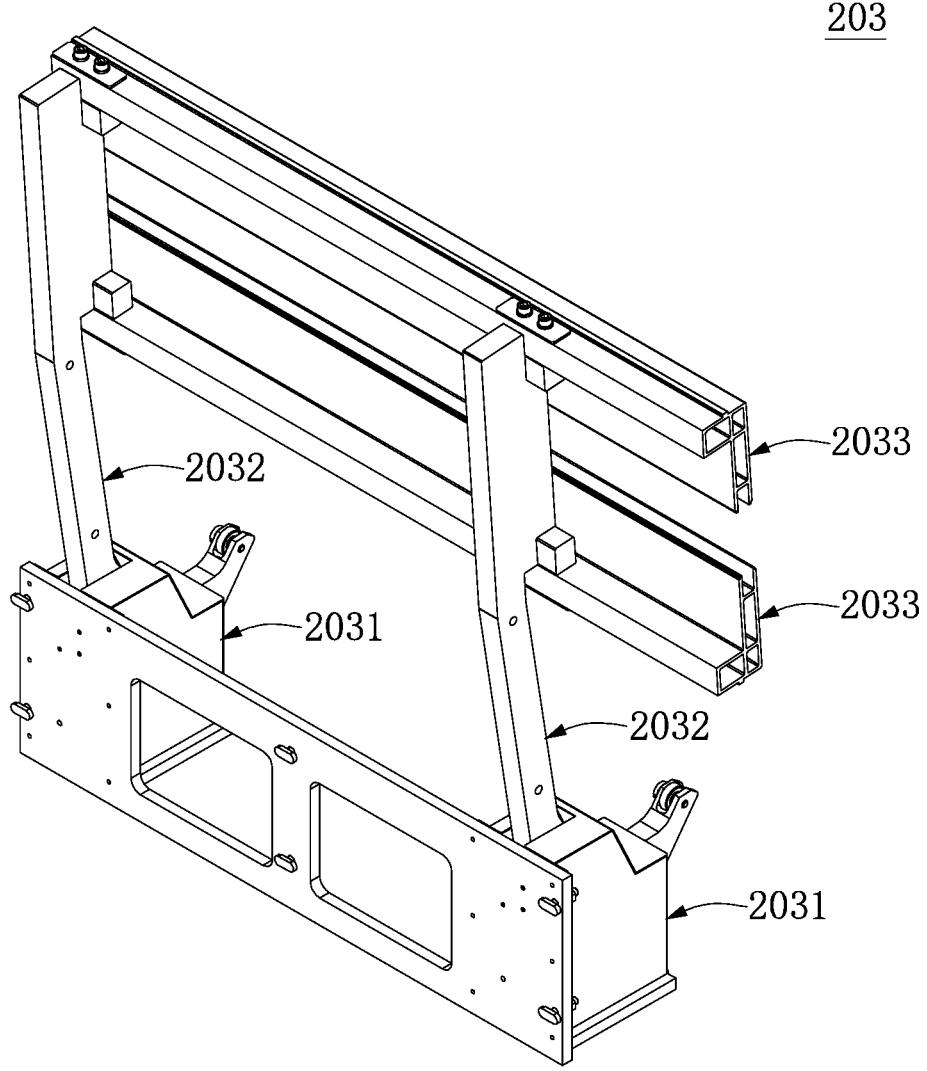
FIG. 5 is a perspective view showing a charging module of FIG. 4.
Figure 6:
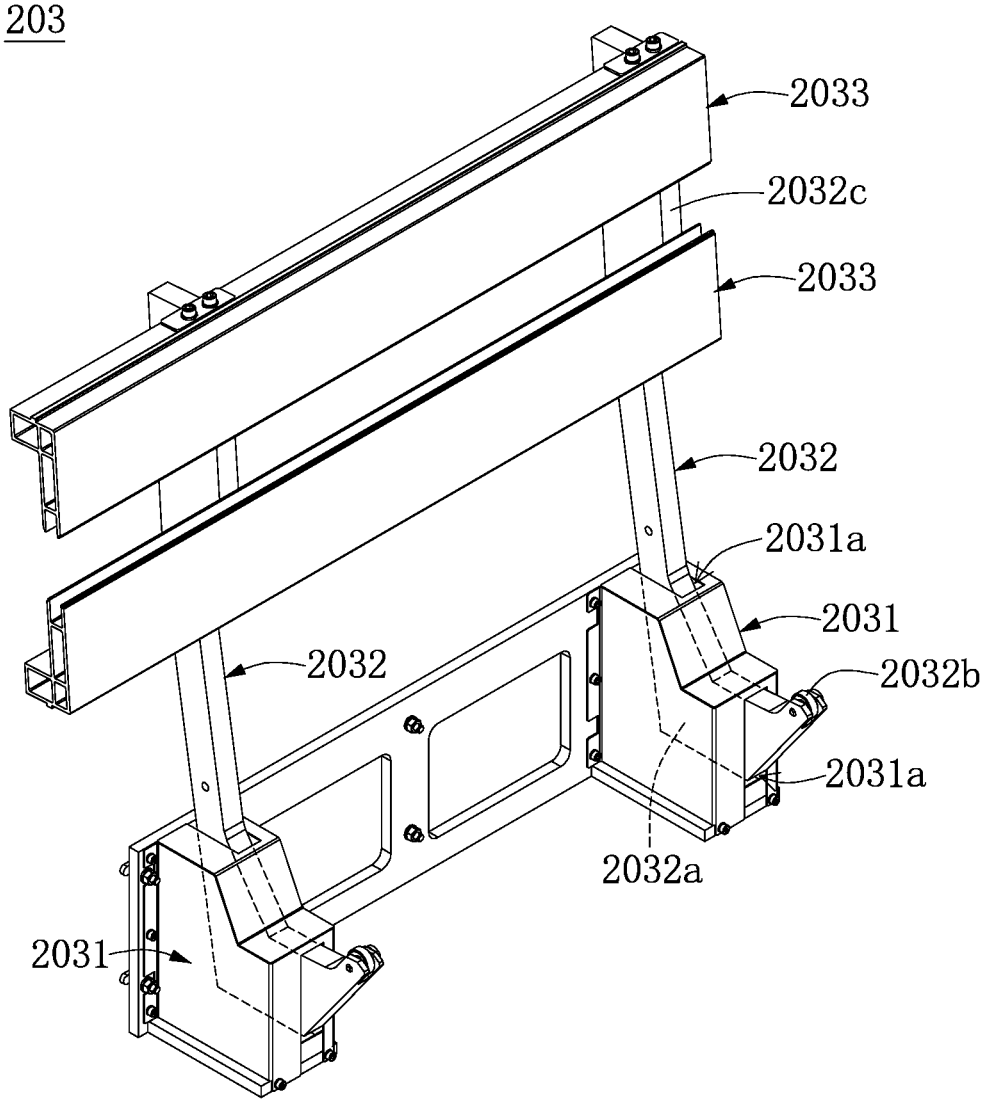
FIG. 6 is a perspective view showing the charging module of FIG. 4 from another perspective.

As shown in FIGS. 4 to 6, the charging module 203 includes at least one fixing seat 2031 fixed on the charging frame 202, at least one adjusting member 2032 installed on the at least one fixing seat 2031, and at least one power emitter 2033 installed on the at least one adjusting member 2032. It should be noted that the number of each of the fixing seat 2031, the adjusting member 2032, and the power emitter 2033 can be changed according to designer demands. For example, the number of each of the fixing seat 2031, the adjusting member 2032, and the power emitter 2033 can be only one. The fixing seat 2031 is fixed on an inner edge of the charging frame 202, and the adjusting member 2032 is configured to change the position of the power emitter 2033.

As shown in FIG. 6, in the present embodiment, the fixing seat 2031 has two elongated openings 2031a, and an inner space of the fixing seat 2031 is in air communication with an outer space through the two openings 2031a. The adjusting member 2032 has a substantial L-shape and includes a pivoting portion 2032a pivotally connected to the fixing seat 2031, a driving portion 2032b extending from the pivoting portion 2032a to one side (i.e., the right side of the pivoting portion 2032a as shown in FIG. 6), and a mounting portion 2032c extending from the pivoting portion 2032a to another side (i.e., the upper side of the pivoting portion 2032a as shown in FIG. 6). In other words, the driving portion 2032b and the mounting portion 2032c respectively extend from the pivoting portion 2032a in two different directions. Moreover, the power emitter 2033 is mounted on the mounting portion 2032c. The pivoting portion 2032a is arranged in the fixing seat 2031. The driving portion 2032b and the mounting portion 2032c are exposed from the fixing seat 2031 by respectively passing through the two openings 2031a. The adjusting member 2032 is rotatable along the pivoting portion 2032a, and the rotating angle of the adjusting member 2032 is limited to the length of the two openings 2031a. The rotating angle of the adjusting member 2032 in the present embodiment is about 5 degrees, but the present disclosure is not limited thereto.

Figure 7:
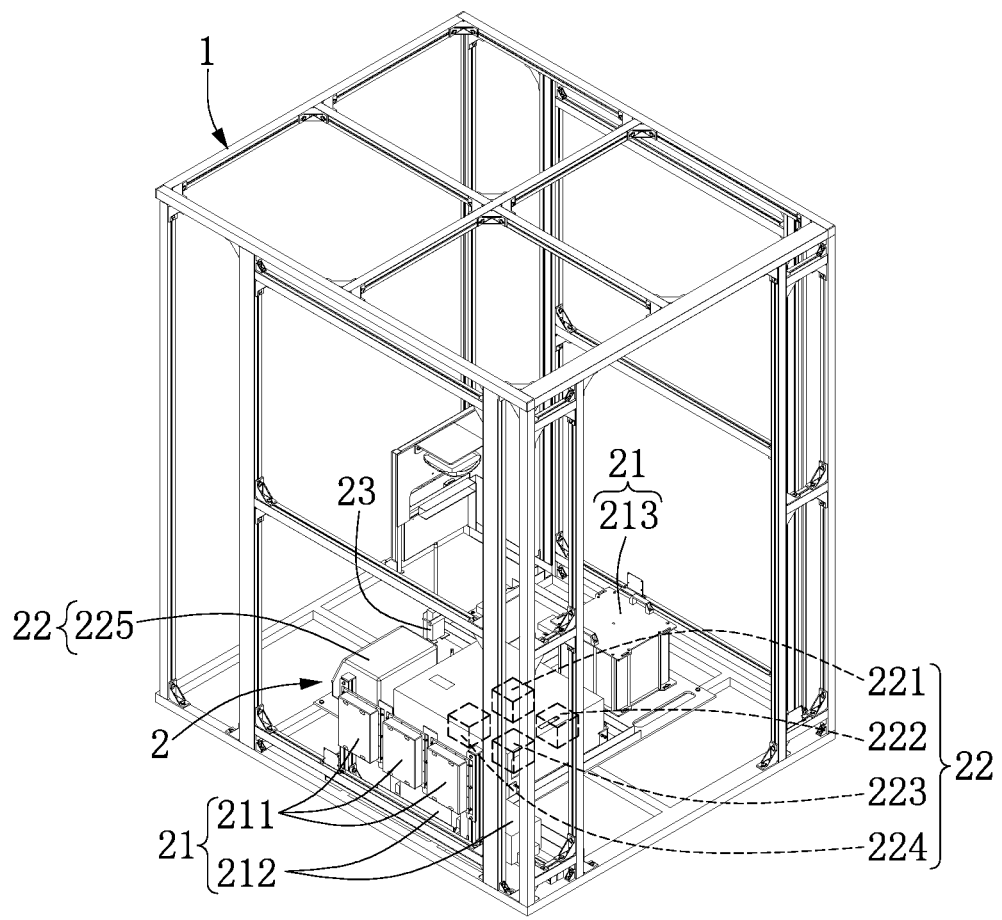
FIG. 7 is a perspective view showing the detecting apparatus according to the present disclosure.
Figure 8:
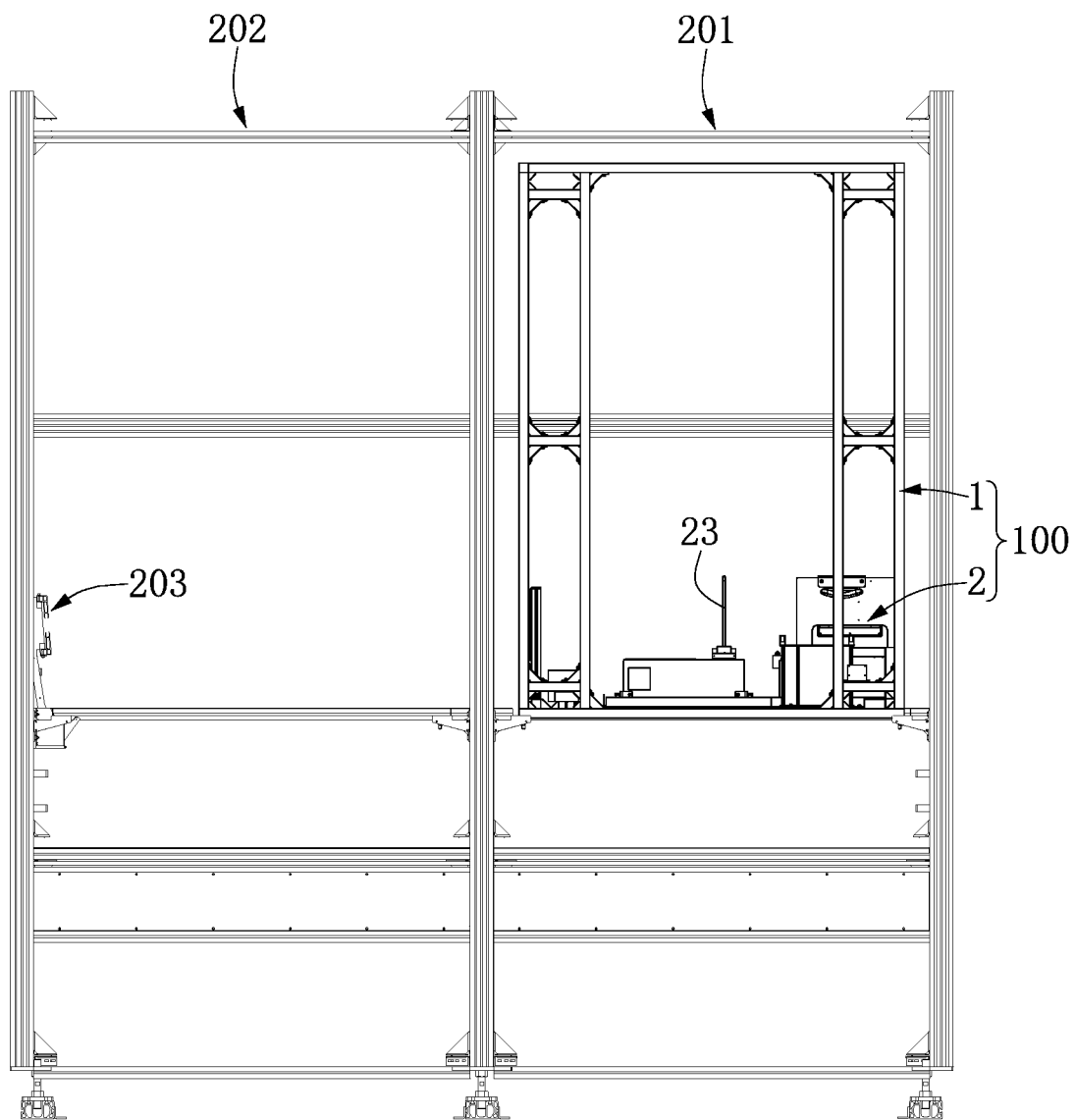
FIG. 8 is a planar view showing the detecting apparatus in the detecting mode.

As shown in FIGS. 7 and 8, the power module 21 includes at least one power receiver 211, an adapter 212 electrically connected to the power receiver 211, and a rechargeable battery 213 electrically connected to the adapter 212. The adapter 212 is configured to transfer energy, which is received by the power receiver 211, to the rechargeable battery 213. The rechargeable battery 213 is configured to provide electricity for operating the detecting apparatus 100 (i.e., the detecting module 22 and the wireless communication module 23).

Figure 9:
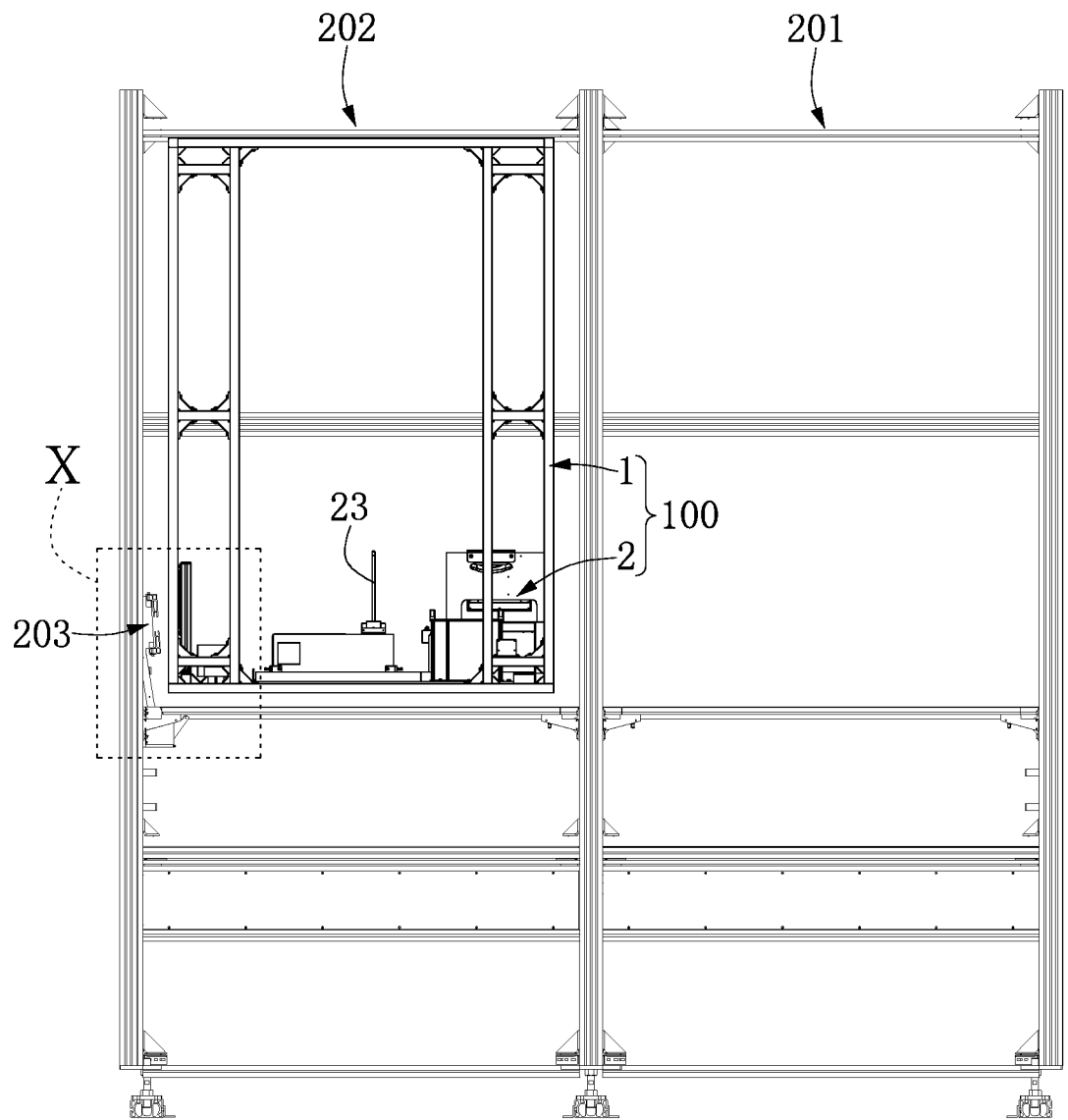
FIG. 9 is a planar view showing the detecting apparatus at an intermediate position.
Figure 10:
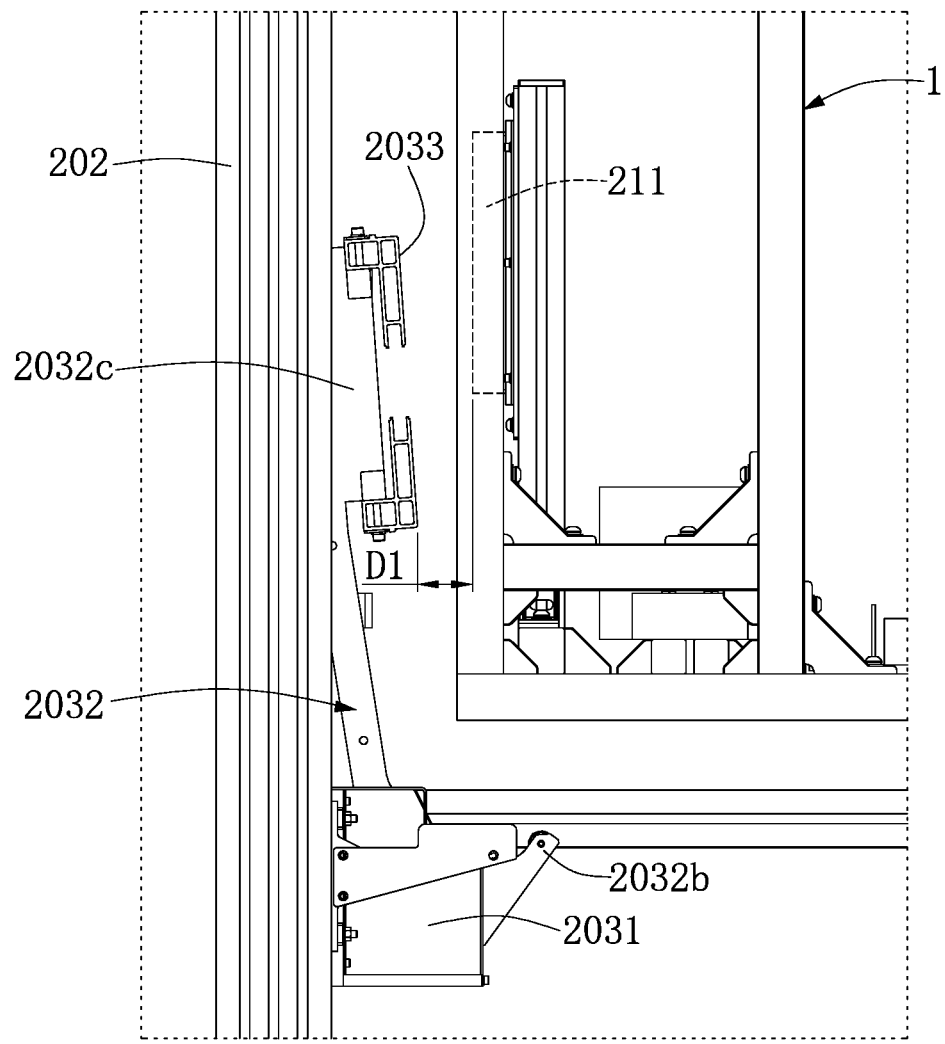
FIG. 10 is an enlarged view showing the portion X of FIG. 9.
Figure 11:
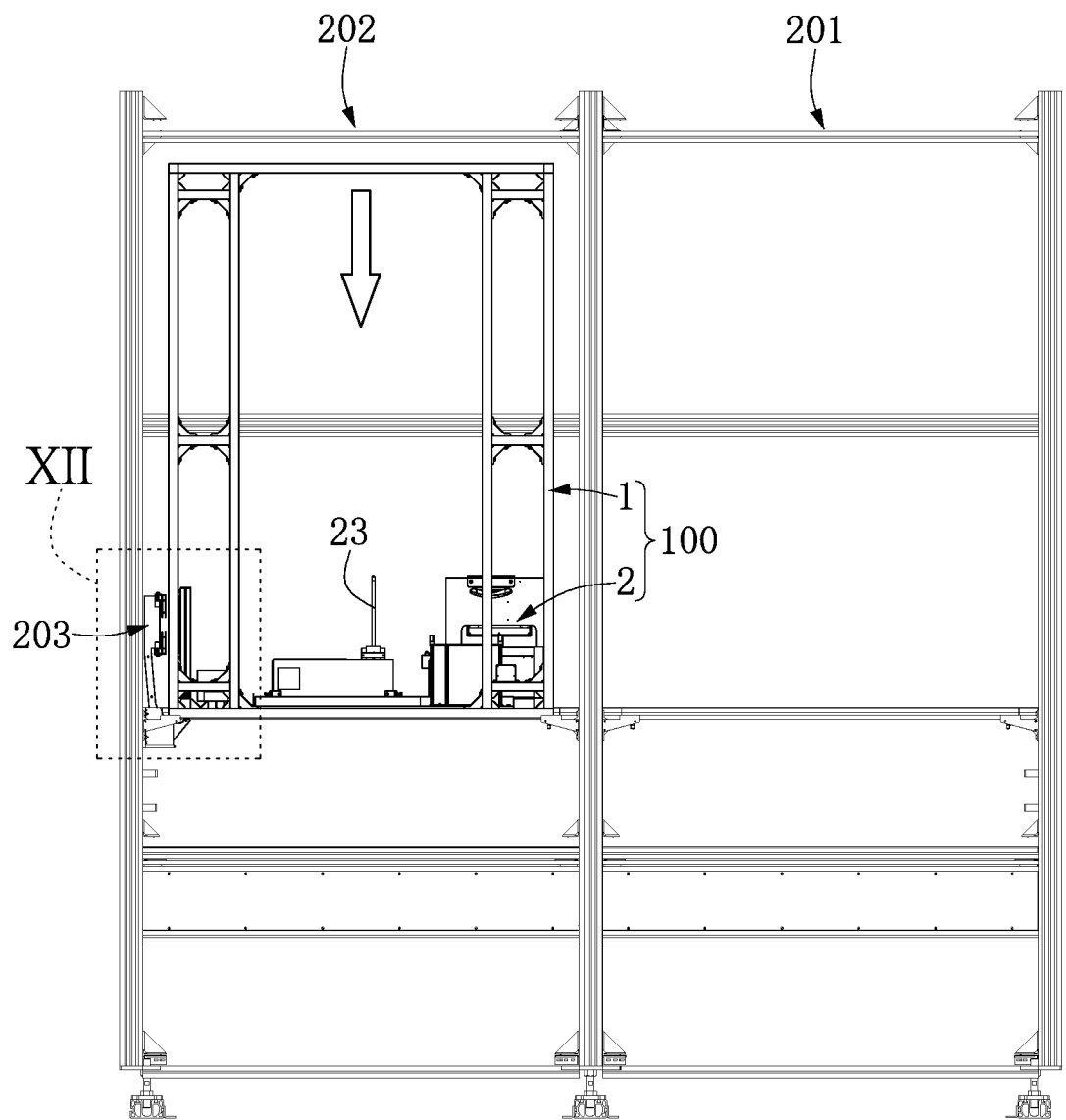
FIG. 11 is a planar view showing the detecting apparatus at a charging position.
Figure 12:
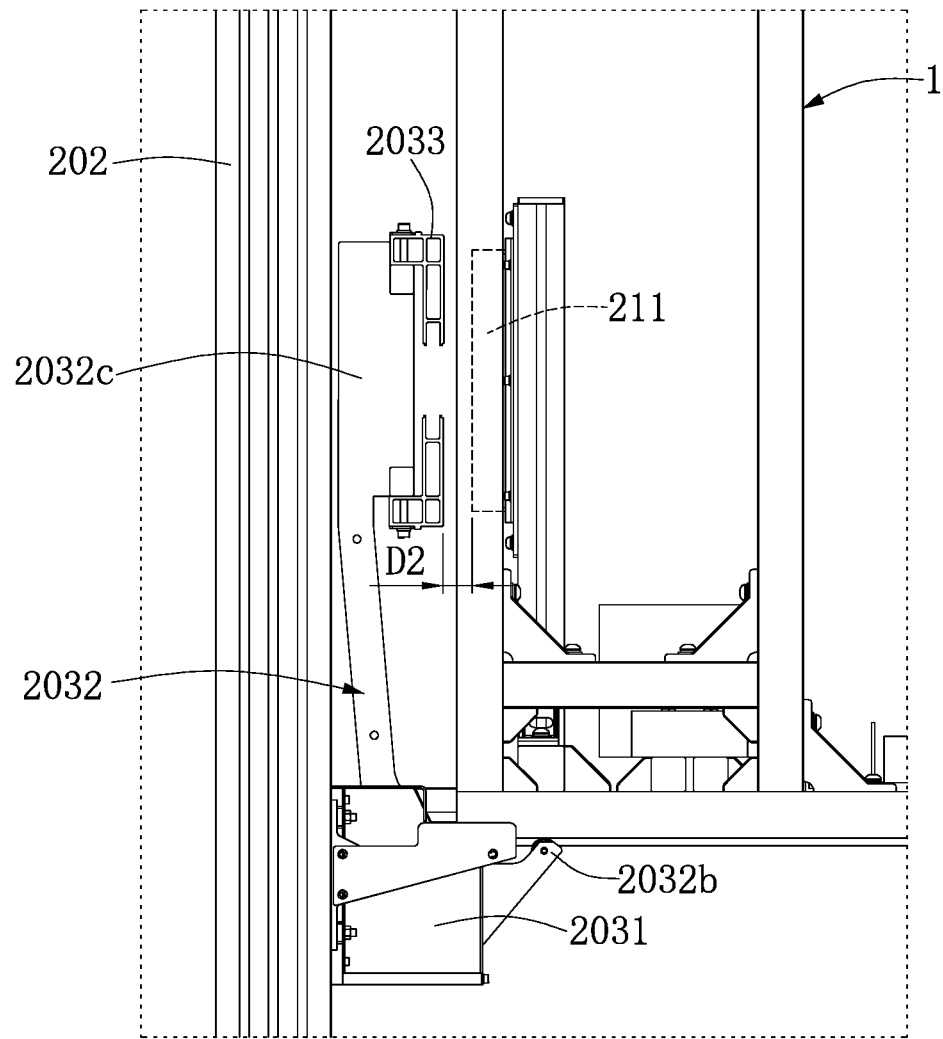
FIG. 12 is an enlarged view showing the portion X II of FIG. 11.

Specifically, when the detecting apparatus 100 enters into the charging frame 202 for being charged, the detecting carrier 1 is moved between an intermediate position (as shown in FIGS. 9 and 10) and a charging position (as shown in FIGS. 11 and 12). That is to say, the detecting carrier 1 is horizontally moved into the charging frame 202 to be located at the intermediate position, and then the detecting carrier 1 is downwardly moved onto the charging frame 202 to be located at the charging position.

As shown in FIGS. 9 and 10, when the detecting carrier 1 is located at the intermediate position, the detecting carrier 1 does not contact the adjusting member 2032 (i.e., the detecting carrier 1 is arranged above the driving portion 2032b of the adjusting member 2032), the power emitter 2033 and the power receiver 211 have a first distance D1, and the power emitter 2033 does not charge the power receiver 211. As shown in FIGS. 11 and 12, when the detecting carrier 1 is located at the charging position, the adjusting member 2032 moves the power emitter 2033 toward the power receiver 211 as abutted against the detecting carrier 1 (i.e., the detecting carrier 1 presses the driving portion 2032b to rotate the adjusting member 2032 so as to move the mounting portion 2032c toward the power receiver 211), the power emitter 2033 and the power receiver 211 have a second distance D2 smaller than the first distance D1, and the power emitter 2033 charges the power receiver 211. The second distance D2 in the present embodiment is approximately 10 mm, but the present disclosure is not limited thereto.

Thus, when the detecting apparatus 100 is in the charging mode, the power receiver 211 of the power module 21 does not contact the power emitter 2033 of the charging module 203 for avoiding generating particles due to a high temperature contact between metals, thereby maintaining the cleanliness of the stock room 200. Moreover, when the detecting carrier 1 is horizontally moved into the charging frame 202, a larger gap (i.e., the first distance D1) is provided between the power receiver 211 and the power emitter 2033 for preventing the power receiver 211 from hitting the power emitter 2033.

The detecting module 22 of the detecting apparatus 100 can be used to detect a variety of environment information (i.e., a cleanliness level, a wind speed and a wind volume, a vibration level, and a concentration of volatile organic compounds), and the following description discloses the possible function and structure of the detecting apparatus 100, but the present disclosure is not limited thereto.

As shown in FIGS. 7 and 8, the detecting module 22 includes a cleanliness detector 221, a wind detector 222, a vibration detector 223, a temperature detector 224, and a VOC detector 225. Specifically, the cleanliness detector 221 is configured to detect a cleanliness level corresponding in position to the detecting carrier 1. The wind detector 222 is configured to detect a wind speed and a wind volume corresponding in position to the detecting carrier 1. The vibration detector 223 is configured to detect a vibration level corresponding in position to the detecting carrier 1. The temperature detector 224 is configured to detect a temperature value of the power receiver 211 when the detecting carrier 1 is located at the charging position. The VOC detector 225 is configured to detect a concentration of volatile organic compounds corresponding in position to the detecting carrier 1. In addition, in other embodiments of the present disclosure, the detecting module 22 can only have the VOC detector 225, or the detecting module 22 be provided with the VOC detector 225 and at least one of the cleanliness detector 221, the wind detector 222, the vibration detector 223, and the temperature detector 224.

Figure 13:
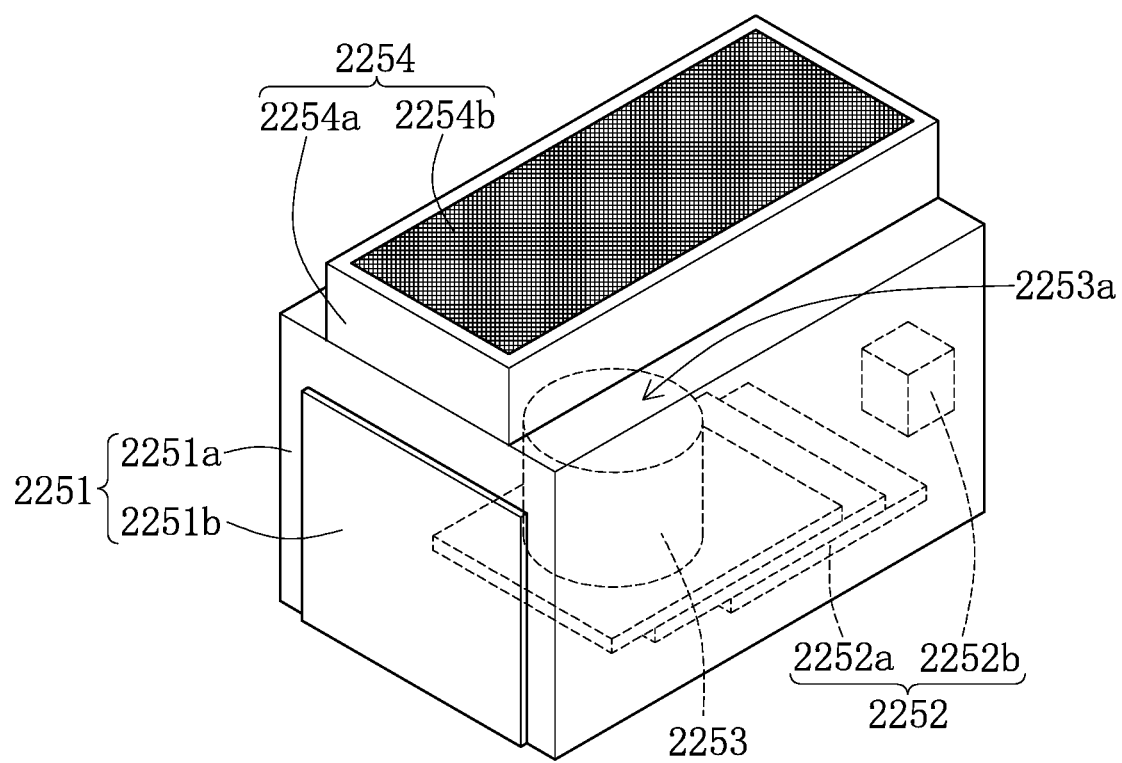
FIG. 13 is a perspective view showing a volatile organic compound (VOC) detector according to the present disclosure.
Figure 14:
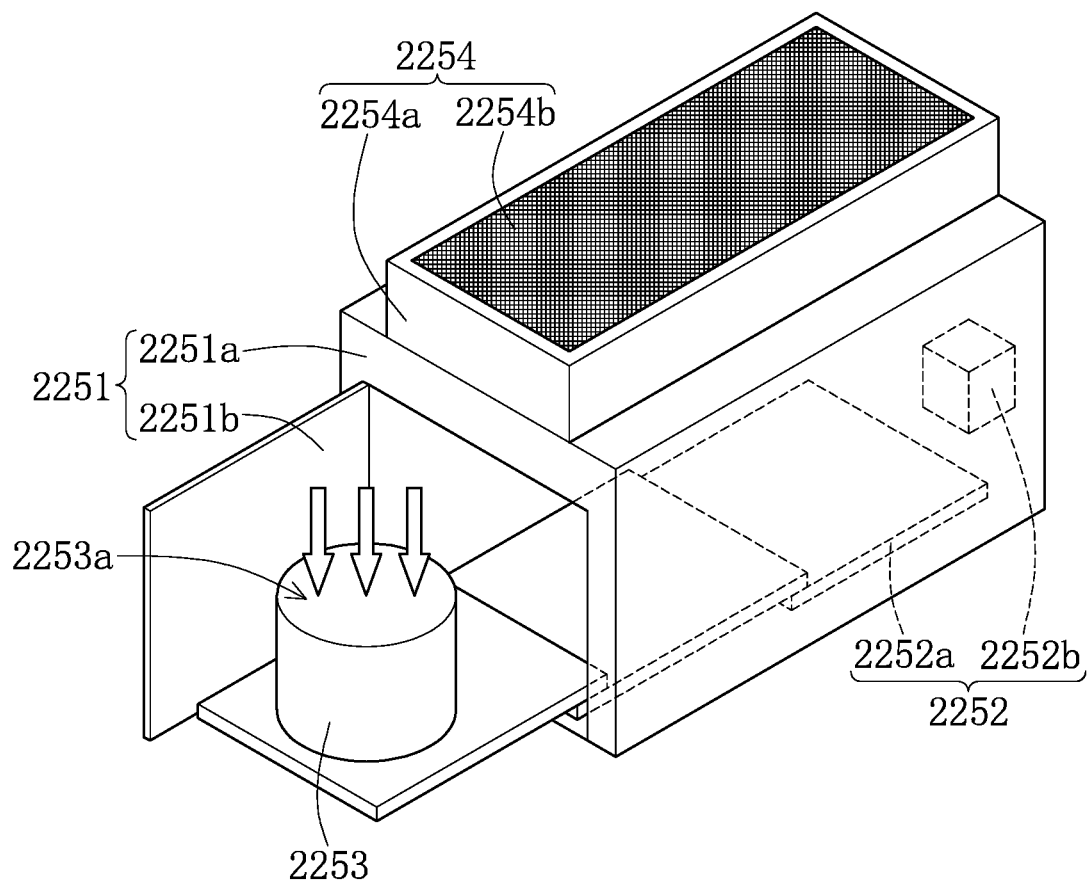
FIG. 14 is a schematic view showing the VOC detector of FIG. 13 in a detecting mode.
Figure 15:
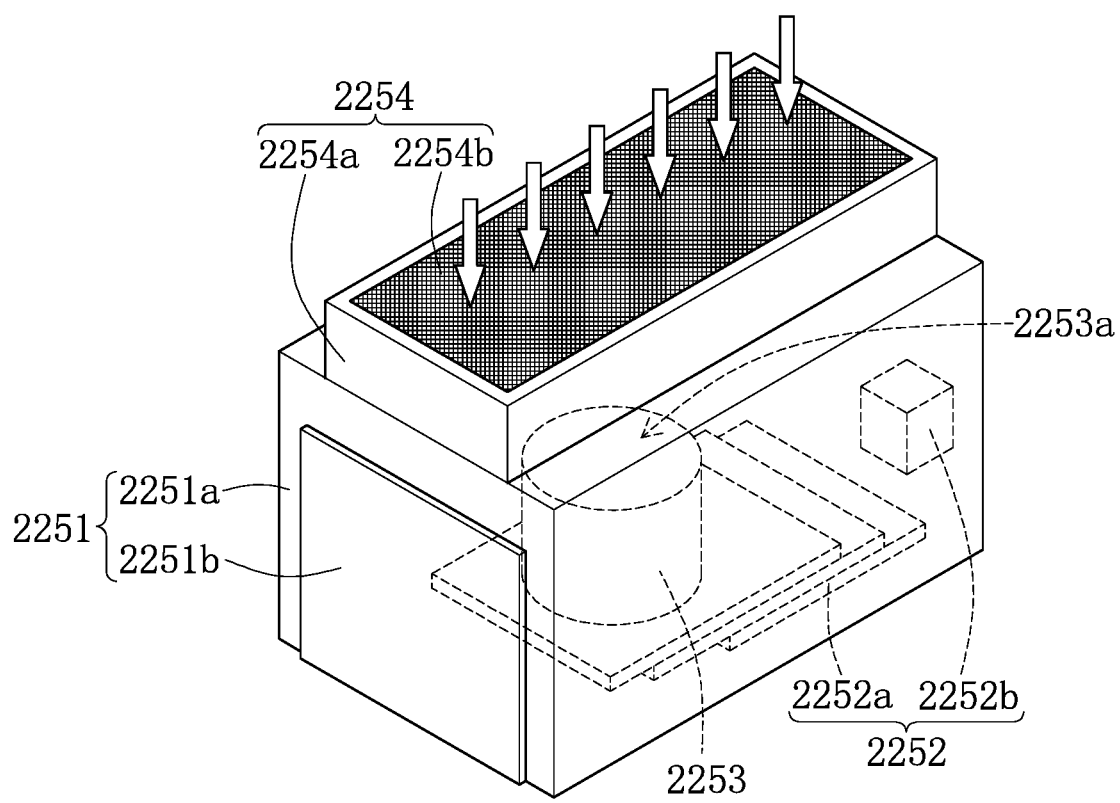
FIG. 15 is a schematic view showing the VOC detector of FIG. 13 in a blowing mode.

As shown in FIGS. 13 to 15, the VOC detector 225 in the present embodiment includes a chassis 2251, a displacement unit 2252 disposed in the chassis 2251, a detecting unit 2253 disposed on the displacement unit 2252, and a blowing unit 2254 disposed on the chassis 2251.

The detecting unit 2253 is movable to be arranged inside or outside the chassis 2251 by using the displacement unit 2252. Specifically, the detecting unit 2253 can be located outside the chassis 2251 (as shown in FIG. 14) for implementing a detecting process and can be located inside the chassis 2251 (as shown in FIG. 15) for implementing a blowing process by using the blowing unit 2254. The blowing process is implemented by using the blowing unit 2254 to blow the detecting unit 2253 for removing volatile organic compounds adhered to the detecting unit 2253, and the blowing unit 2254 in the present embodiment is configured to remove at least 90% of the volatile organic compounds adhered to the detecting unit 2253, but the present disclosure is not limited thereto. Moreover, at least one blowing process is implemented between any two detecting processes, thereby improving the accuracy of each detecting process implemented by the detecting unit 2253.

Specifically, the chassis 2251 includes a box 2251a and a door 2251b pivotally connected to the box 2251a. The door 2251b is preferably provided with a position resetting member (e.g., a spring), such that after the door 2251b is opened by a force, the door 2251b can return to the initial position when the force disappears. The displacement unit 2252 includes a stretching member 2252a and a driving member 2252b (e.g., a controller) electrically connected to the stretching member 2252a. The detecting unit 2253 is disposed on the stretching member 2252a, and the stretching member 2252a is driven by the driving member 2252b to open the door 2251b and to move the detecting unit 2253 to be arranged outside the box 2251a. The stretching member 2252a in the present embodiment moves the detecting unit 2253 in a straight direction, but the present disclosure is not limited thereto. For example, in other embodiments of the present disclosure, the stretching member 2252a can move the detecting unit 2253 in a curved direction. The detecting unit 2253 has a detecting surface 2253a preferably facing the blowing unit 2254, and the detecting surface 2253a is configured to capture volatile organic compounds.

The blowing unit 2254 in the present embodiment is a fan filter unit (FFU). In other words, the blowing unit 2254 includes a fan 2254a disposed on the chassis 2251 and a filter 2254b disposed on the fan 2254a and exposed from the chassis 2251. The fan 2254a is configured to inhale an external air through the filter 2254b so as to blow the detecting surface 2253a of the detecting unit 2253, and the filter 2254b is configured for filtering volatile organic compounds mixed in the external air, thereby at least 90% of the volatile organic compounds adhered to the detecting surface 2253a of the detecting unit 2253 can be removed.

In addition, the blowing process of the detecting unit 2253 in the present embodiment is implemented in the chassis 2251, but the present disclosure is not limited thereto. For example, in other embodiments of the present disclosure, the blowing process of the detecting unit 2253 can be implemented outside the chassis 2251.

In summary, the detecting apparatus 100 in the present embodiment is provided with the VOC detector 225 for detecting the concentration of volatile organic compounds in the stock room 200. Moreover, after each detecting process of the VOC detector 225 is implemented, the volatile organic compounds adhered to the VOC detector 225 can be approximately removed by the blowing unit 2254, thereby improving the accuracy of the follow-up detecting process of the detecting unit 2253.

The descriptions illustrated supra set forth simply the preferred embodiments of the present disclosure; however, the characteristics of the present disclosure are by no means restricted thereto. All changes, alterations, or modifications conveniently considered by those skilled in the art are deemed to be encompassed within the scope of the present disclosure delineated by the following claims.

What is claimed is:
1. A detecting apparatus for being movably arranged in a stock room having a charging frame and a plurality of storing frames, comprising:
   a detecting carrier configured for being transported into the charging frame or anyone of the storing frames; and
   a detecting device installed in the detecting carrier and including:
      a power module configured to provide electricity for operating the detecting apparatus; and
      a detecting module including a volatile organic compound (VOC) detector, wherein the VOC detector includes:
         a chassis comprising a box and a door installed on the box;
         a displacement unit disposed in the chassis;
         a detecting unit disposed on the displacement unit and configured to detect the concentration of volatile organic compounds corresponding in position to the detecting carrier, wherein the detecting unit is movable to be arranged inside or outside the box by using the displacement unit; and
         a blowing unit disposed on the chassis, wherein the blowing unit is configured to blow the detecting unit for removing at least part of volatile organic compounds adhered to the detecting unit.

2. The detecting apparatus as claimed in claim 1, wherein the blowing unit includes a fan disposed on the chassis and a filter disposed on the fan and exposed from the chassis, the fan is configured to inhale an external air through the filter so as to blow the detecting unit, and the filter is configured for filtering volatile organic compounds mixed in the external air.

3. The detecting apparatus as claimed in claim 2, wherein the blowing unit is configured to remove at least 90% of the volatile organic compounds adhered to the detecting unit.

4. The detecting apparatus as claimed in claim 1, wherein the displacement unit includes a stretching member and a driving member electrically connected to the stretching member, the detecting unit is disposed on the stretching member, and the stretching member is driven by the driving member to open the door and to move the detecting unit to be arranged outside the box.

5. The detecting apparatus as claimed in claim 1, wherein the detecting unit has a detecting surface facing the blowing unit, and the detecting surface is configured to capture volatile organic compounds.

6. The detecting apparatus as claimed in claim 1, wherein the detecting unit is configured to be arranged outside the chassis for implementing a detecting process and is configured to be arranged inside the chassis for implementing a blowing process by using the blowing unit, and at least one blowing process is implemented between any two detecting processes.

7. The detecting apparatus as claimed in claim 1, wherein the detecting module includes a cleanliness detector, a wind detector, and a vibration detector; the cleanliness detector is configured to detect a cleanliness level corresponding in position to the detecting carrier, the wind detector is configured to detect a wind speed and a wind volume corresponding in position to the detecting carrier, and the vibration detector is configured to detect a vibration level corresponding in position to the detecting carrier.

8. A volatile organic compound (VOC) detector, comprising:
   a chassis comprising a box and a door installed on the box;
   a displacement unit disposed in the chassis;
   a detecting unit disposed on the displacement unit and configured to detect the concentration of volatile organic compounds, wherein the detecting unit is movable to be arranged inside or outside the box by using the displacement unit; and
   a blowing unit disposed on the chassis, wherein the blowing unit is configured to blow the detecting unit for removing at least part of volatile organic compounds adhered to the detecting unit.

9. The VOC detector as claimed in claim 8, wherein the blowing unit includes a fan disposed on the chassis and a filter disposed on the fan and exposed from the chassis, the fan is configured to inhale an external air through the filter so as to blow the detecting unit, and the filter is configured for filtering volatile organic compounds mixed in the external air.

10. The VOC detector as claimed in claim 8, wherein the displacement unit includes a stretching member and a driving member electrically connected to the stretching member, the detecting unit is disposed on the stretching member, and the stretching member is driven by the driving member to open the door and to move the detecting unit to be arranged outside the box.

* * * * *